US008967427B2

(12) United States Patent
Hogan

(10) Patent No.: US 8,967,427 B2
(45) Date of Patent: Mar. 3, 2015

(54) PORTABLE EYE PROTECTION SYSTEM AND METHOD

(76) Inventor: Christine K. Hogan, Topeka, KS (US)

( * ) Notice: Subject to any disclaimer, the term of this patent is extended or adjusted under 35 U.S.C. 154(b) by 273 days.

(21) Appl. No.: 13/607,010

(22) Filed: Sep. 7, 2012

(65) Prior Publication Data

US 2014/0068827 A1 Mar. 13, 2014

(51) Int. Cl.
B65D 83/08 (2006.01)
A61F 9/04 (2006.01)

(52) U.S. Cl.
CPC .............. B65D 83/0847 (2013.01); A61F 9/04 (2013.01)
USPC ............................................ 221/45; 221/309

(58) Field of Classification Search
CPC ........... A61F 9/04; A61F 13/12; A61F 9/045; B65D 83/0847; B65D 83/0876; B65D 83/12
USPC ........................................ 221/45, 71, 309, 63
See application file for complete search history.

(56) References Cited

U.S. PATENT DOCUMENTS

| | | | |
|---|---|---|---|
| 1,930,972 A | 10/1933 | Griswold et al. | |
| 2,165,668 A | 7/1939 | Vaccaro | |
| 2,874,385 A | 2/1959 | Wade | |
| 3,619,815 A | 11/1971 | Towner | |
| 3,677,866 A | 7/1972 | Pickett et al. | |
| 4,645,077 A * | 2/1987 | McLaughlin et al. | 206/449 |
| 4,701,962 A | 10/1987 | Simon | |
| 4,719,909 A * | 1/1988 | Micchia et al. | 128/858 |
| 4,793,002 A * | 12/1988 | Simon | 2/15 |
| 4,947,990 A * | 8/1990 | Klemets | 206/409 |
| 4,979,811 A | 12/1990 | Boyer | |
| 5,263,200 A | 11/1993 | Miller | |
| 5,417,345 A | 5/1995 | Smith | |
| 5,970,515 A | 10/1999 | Fishbaugh | |
| 6,131,208 A | 10/2000 | Banks | |
| 6,454,096 B1 * | 9/2002 | Kondoh et al. | 206/494 |
| 6,571,799 B1 | 6/2003 | Daly | |
| 6,789,271 B2 | 9/2004 | Banks | |
| 6,984,037 B2 | 1/2006 | Bleau | |
| 7,052,130 B2 * | 5/2006 | Fishbaugh | 351/44 |
| 7,188,946 B2 | 3/2007 | Bleau | |
| RE39,896 E * | 10/2007 | Arnold et al. | 602/54 |
| 7,275,819 B2 | 10/2007 | Bleau | |
| 7,413,302 B2 | 8/2008 | Kroll et al. | |
| 7,458,456 B2 * | 12/2008 | Hogan et al. | 206/5 |
| 7,496,968 B2 | 3/2009 | Head | |
| 2011/0163110 A1 | 7/2011 | Lehmann | |

FOREIGN PATENT DOCUMENTS

EP 0998887 A1 5/2000
WO 2005/082721 A2 9/2005

OTHER PUBLICATIONS

Search Report and Written Opinion from related PCT Patent Application No. PCT/US2013/058429; Applicant: Christine K. Hogan; Dated: Dec. 11, 2013; 12 pages.

(Continued)

*Primary Examiner* — Timothy Waggoner
(74) *Attorney, Agent, or Firm* — Hovey Williams LLP

(57) ABSTRACT

A portable eye protection system and method is disclosed. The eye protection system includes a dispensing case and substantially flat eyewear articles received therein. The eyewear articles include at least one eye cover and a backing. The eye cover can be shifted into an eye-covering configuration to protect a user's eye.

13 Claims, 3 Drawing Sheets

(56) References Cited

OTHER PUBLICATIONS https://www.pipromos.com/Content/images/prod/HEALTH/HEALTH_40071_Z.jpg, Caring Family Pharmacy, 1 page, Apr. 24, 2012.

http://www.imprintelephant.com/popup_image.php?pID=741&PHPSESSID-rhq07bvmttrt0r912h2hqh8ea0, Nuvo Bandage Dispenser with Colored Bandage, 1 page, Apr. 24, 2012.

* cited by examiner

PORTABLE EYE PROTECTION SYSTEM AND METHOD

FIELD OF THE INVENTION

This invention relates generally to eyewear. More particularly, the invention relates to portable protective eyewear and methods for protecting a human eye.

BACKGROUND OF THE INVENTION

When exposed to natural or artificial sunlight, it is beneficial to use protective eyewear to limit the amount of light that reaches a user's eyes. Conventional sunglasses may be used to effectively limit the amount of light reaching a user's eyes, but the frames of the sunglasses may create an undesirable tan pattern. For this and other reasons, pairs of individual lenses, with each lens adapted to cover one eye of the user, have been adopted to provide eye protection while minimizing undesirable tan patterns. However, current individual lenses can be lost or damaged while being stored and/or transported. Furthermore, current individual lenses can be improved upon to provide increased functionality. Accordingly, there is a need for an improved portable eye protection system that can securely and conveniently transport individual lenses and provide eyewear with increased functionality.

SUMMARY OF THE INVENTION

In one embodiment of the present invention, a portable eye protection system is provided which includes a dispensing case including a main housing having an opening at one end thereof, and a plurality of substantially flat, individually-dispensable eyewear articles received in the dispensing case and configured for individual manual removal from the main housing through the opening. Each of the individually-dispensable articles includes a backing and an eye cover removably attached to the backing. The eye cover is configured to be shifted from a substantially flat configuration into a substantially concave eye-covering configuration when the eye cover is removed from the backing.

In another embodiment of the present invention, a portable eye protection system is provided which includes a plurality of substantially flat, individually-dispensable eyewear articles. Each of the articles includes a backing and an eye cover removably attached to the backing, the eye cover having an edge and a central portion. The eye cover includes a scission radially extending from the central portion to the edge. The eye cover further includes a film and an adhesive coated onto the film, where at least a portion of the adhesive adheres the backing to the eye cover when the eye cover is attached to the backing. The eye cover is configured to be shifted from a substantially flat configuration into a substantially concave eye-covering configuration when the eye cover is removed from the backing, where at least a portion of the adhesive maintains the eye cover in the eye-covering configuration. The portable eye protection system further includes a dispensing case configured to receive the eyewear articles in a stacked configuration, the case having an opening that provides access to at least one article so that the one article can be manually contacted and slid through the opening while the other articles are retained within the case.

In yet another embodiment of the present invention, an eye protection method is provided that includes (a) sliding a first eyewear article through an opening in an eyewear dispensing case holding at least five individual eyewear articles in a stacked configuration, (b) removing a backing of the first eyewear article from an eye cover of the first eyewear article, (c) manipulating the eye cover from a substantially flat configuration to a substantially concave configuration, and (d) covering a human eye with the eye cover while the eye cover is maintained in the concave configuration.

BRIEF DESCRIPTION OF THE FIGURES

Embodiments of the present invention are described herein with reference to the following drawing figures, wherein.

DETAILED DESCRIPTION

The following detailed description of the present invention references various embodiments. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 1:
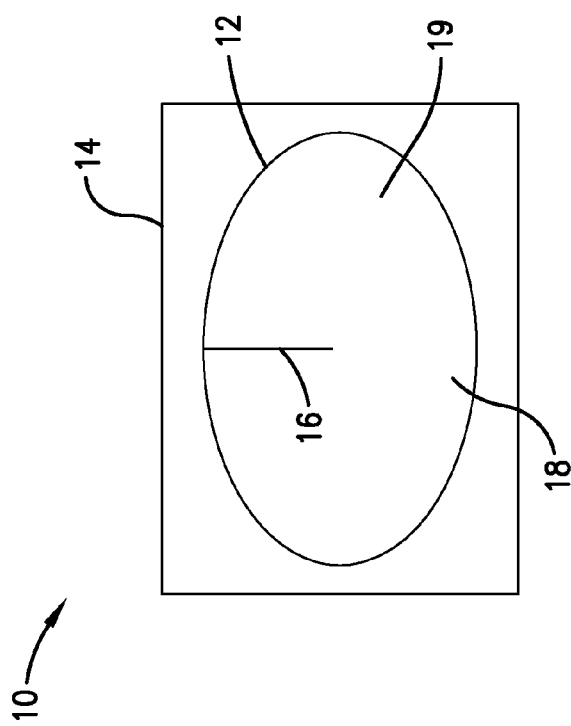
FIG. 1 is a plan view of an eyewear article in accordance with one embodiment of the present invention, particularly illustrating an elliptical eye cover and a rectangular backing member attached to the eye cover.

FIG. 1 depicts an eyewear article 10 in accordance with one embodiment of the present invention. It should be understood that FIG. 1 depicts just one embodiment of an eyewear article, and that a wide variety of embodiments of eyewear articles are contemplated by the present invention. The eyewear article of FIG. 1 will now be described in detail.

The eyewear article 10 of FIG. 1 is in a substantially flat configuration. The eyewear article 10 includes an eye cover 12 and a backing 14. The eye cover 12 may include a scission 16 extending along a portion thereof. The eye cover 12 can be made from any type of material suitable for protecting a human eye, and a particular material can be selected based on the protection desired.

In certain embodiments, the eye cover 12 can include a flexible material, such as, for example, a film 18. There are numerous types of films that could be used in various embodiments of the present invention. For example, the eye cover 12 could include a film 18 that is a single layer film or a multiple layer film laminate. In certain embodiments, the film 18 can have a thickness of at least 0.00005 inches, 0.0001 inches, or 0.0005 inches and/or not more than 0.05 inches, 0.01 inches, or 0.001 inches.

In certain embodiments, the eye cover 12 can block at least a portion of ultraviolet (UV) radiation from contacting the user's eyes. In one embodiment, the eye cover 12 includes a UV blocking film. UV blocking films are well known in the art and are commercially available in a variety of types. For example, a UV blocking film can be, in part, made of a UV absorbing polymeric material. Other types of films exhibit UV blocking ability by incorporating UV absorbing materials into the film or coating them onto the film. Yet other types of films exhibit UV blocking ability due to the presence of an adhesive, containing UV absorbing compounds, which is applied between the layers of a multiple layer film laminate. In one embodiment, the eye cover 12 may include more than one type of UV blocking film.

In certain embodiments, the eye cover 12 can block at least a portion of radiation in the range of from 200 nanometers to 400 nanometers. The eye cover 12 may have a spectral transmittance value at or below 0.001 over the wavelength range of from 200 nanometers to 320 nanometers and/or a spectral transmittance value at or below 0.01 over the wavelength range of from 320 nanometers to 400 nanometers. The spectral transmittance value is defined as the spectral irradiance transmitted through the eye cover 12 divided by the spectral irradiance incident on the eye cover 12. The spectral irradiance is defined as the irradiance resulting from radiation within a wavelength range as the range becomes vanishingly small, expressed in units of watts per square centimeter per nanometer ($W/(cm^2/nm)$).

The eye cover 12 may be opaque, transparent, or translucent. In certain embodiments, the eye cover 12 may transmit a portion of visible light so that the user can see through the eye cover 12 when placed over the user's eye. In one embodiment, the eye cover 12 may have a spectral transmittance value of greater than 0.01 for wavelengths greater than 400 nanometers. In another embodiment, the eye cover 12 may have a spectral transmittance value of greater than 0.01 for wavelengths greater than 400 nanometers and also block at least a portion of radiation having a wavelength of from 200 nanometers to 400 nanometers. In yet another embodiment, the eye cover 12 may: have a spectral transmittance value at or below 0.001 over the wavelength range of from 200 nanometers to 320 nanometers; have a spectral transmittance value at or below 0.01 over the wavelength range of from 320 nanometers to 400 nanometers; or have a spectral transmittance value greater than 0.01 for wavelengths greater than 400 nanometers, or any combination thereof.

Returning now to FIG. 1, the eye cover 12 may be removably attached to the backing 14 in a variety of ways. For example, in certain embodiments, the eye cover 12 may be removably attached to the backing 14 via an adhesive 19 coated onto the film 18. The adhesive 19 can be any type of adhesive that is suitable for safely contacting human skin. In certain embodiments, the adhesive 19 can include a pressure sensitive adhesive. In one embodiment, the adhesive 19 is coated onto at least one side of the film 18, such as, for example, the side of the film 18 that is in contact with the backing 14. In another embodiment, an adhesive 19 coated onto the film 18 remains thereon after a user manually peels the film 18 from the backing 14.

The backing 14 can be made from any type of material that is suitable to provide a flat surface to removably attach to and store the eye cover 12. In certain embodiments, the backing 14 can include a paper material. In other embodiments, the paper material may be coated with a polymer, wax, or any other material that can provide a smooth surface to enhance the removability of the eye cover 12 from the backing 14. In one embodiment, the backing 14 can include a plastic material.

In the embodiment depicted in FIG. 1, the backing 14 is substantially rectangular in shape. Other shapes are also contemplated by the present invention, such as, for example, the backing 14 may be substantially oval in shape. In other embodiments, the backing 14 may be substantially the size and shape of a region of the film 18 coated with an adhesive 19.

Figure 2:
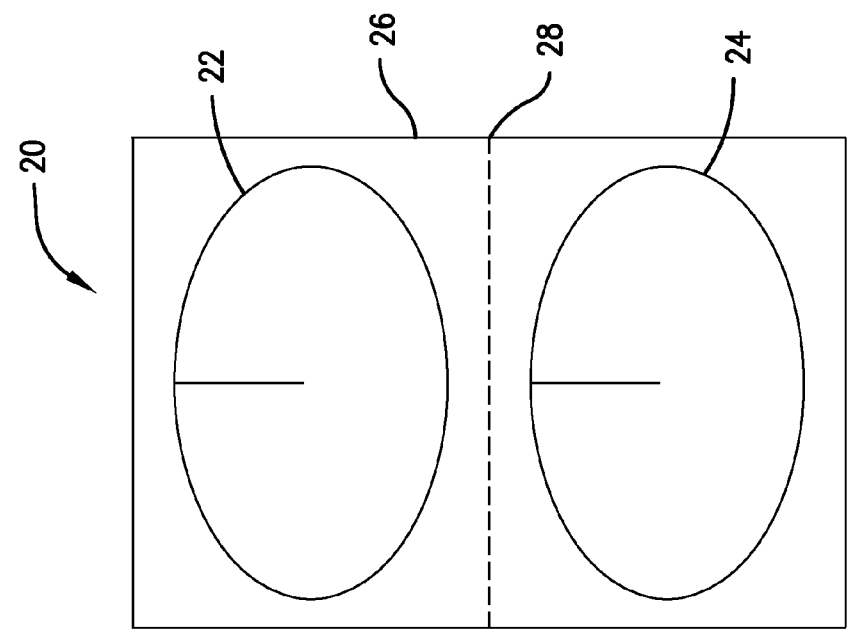
FIG. 2 is a plan view of an eyewear article in accordance with another embodiment of the present invention, particularly illustrating two elliptical eye covers on a single backing member.

FIG. 2 depicts another embodiment of an eyewear article 20, which includes two eye covers 22 and 24 removably attached to the same side of one backing 26. In one embodiment, the eye covers 22 and 24 are attached to opposite sides of the backing 26. Other configurations of eyewear articles are also contemplated by the present invention, such as, for example, eyewear articles including four, six, or eight eye covers removably attached to one backing. The eye covers 22 and 24 and the backing 26 may have the same variations and parameters as described for the eye cover 12 and backing 14 of FIG. 1.

The backing 26 may include a fold line 28. In certain embodiments, the fold line 28 may include a line of weakness. The line of weakness could be formed in a variety of manners, such as, for example, by perforating the backing 26 along the fold line 28. In other embodiments, the fold line 28 may include a line marked on the backing 26 to guide a user to fold the eyewear article 20 along that line.

Figure 3:
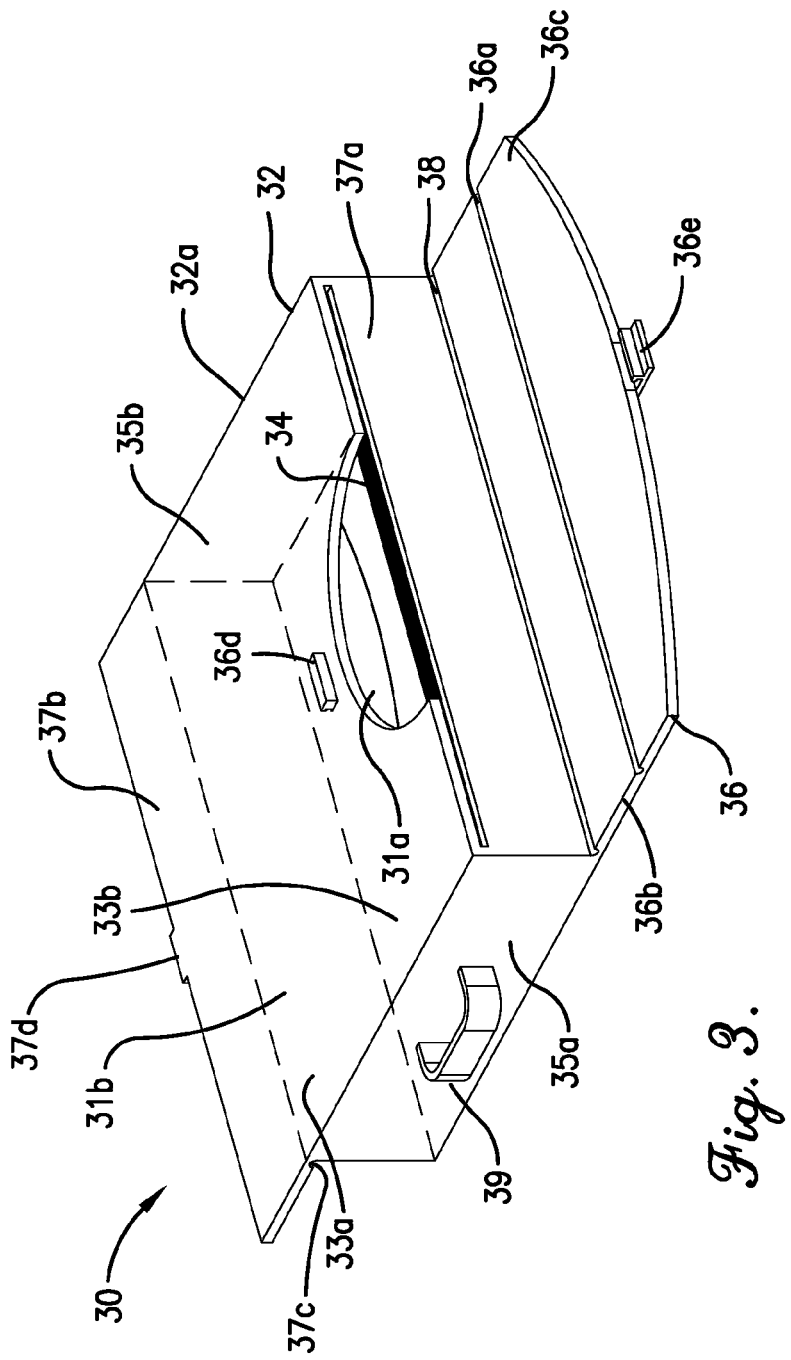
FIG. 3 is a perspective view of an eye protection system in accordance with one embodiment of the present invention, particularly illustrating a dispensing case that includes two lids and a stack of eyewear articles in a substantially flat configuration received inside the case.

FIG. 3 depicts one embodiment of an eye protection system 30 in accordance with the present invention. The eye protection system 30 includes a dispensing case 32 holding a stack of substantially flat eyewear articles 34 therein.

The dispensing case 32 includes a main housing 32a having two openings 31a and 31b at opposing ends thereof. The main housing 32a includes: a top face 33a and an opposing bottom face 33b; a pair of opposing sidewalls 35a and 35b; and an end wall 37a. The main housing 32a of the dispensing case 32 has a thickness, measured between the top face 33a and the bottom face 33b of less than 1 inch, 0.75 inches, or 0.5 inches. The top face 33a and bottom face 33b each can have an area of less than 5 square inches, 4 square inches, or 3 square inches. In certain embodiments, the top face 33a and the bottom face 33b are substantially rectangular in shape. While not depicted in FIG. 3, a variety of configurations for the dispensing case 32 are contemplated by this invention, such as, for example, the top face 33a and the bottom face 33b can be substantially oval in shape.

The opening 31a may be cooperatively defined by the top face 33a and the end wall 37a. In other embodiments, the opening 31a is at least partly or entirely defined by the top face 33a. In another embodiment, the opening 31a is at least partly or entirely defined by the end wall 37a.

In certain embodiments, the dispensing case 32 can include a lid 36. The lid 36 can be shifted between an open configuration, where the lid 36 permits access to at least a portion of the opening 31a, and a closed configuration, where the lid 36 substantially blocks the opening 31a. In one embodiment, the dispensing case 32 does not include a lid 36.

The lid 36 may be coupled to the main housing 32a in any manner that is suitable for use in accordance with the present invention and can be selected by one skilled in the art. In certain embodiments, the lid 36 can be coupled to the main housing 32a by a hinge 38, which can be a living hinge. In one or more embodiments, the lid 36 may not be fixedly coupled to the main housing 32*a*, e.g., the lid 36 may be entirely separated from the main housing 32*a* when in an open configuration.

In certain embodiments, the lid 36 can include a living hinge 36*a*, which contacts two lid portions 36*b* and 36*c*. When the lid 36 is in the closed configuration, the living hinge 36*a* allows the two lid portions 36*b* and 36*c* to block at least a portion of the opening 31*a* that is cooperatively defined by both the top face 33*a* and the end wall 37*a*. For example, when in the closed configuration, lid portion 36*b* would block at least a portion of the opening 31*a* that is defined by the end wall 37*a* and the lid portion 36*c* would block at least a portion of the opening 31*a* that is defined by the top face 33*a*.

In certain embodiments, the main housing 32*a* may include an attachment element 36*d* for maintaining the lid 36 in a closed configuration. The attachment element 36*d* can be any suitable element for attaching the lid 36 to the main housing 32*a*, as determined by one skilled in the art. For example, in one embodiment, the attachment element 36*d* may include a notch in the top face 33*a* that can receive a complimentary portion 36*e* of the lid 36, when the lid 36 is in the closed configuration.

The opening 31*b* of the dispensing case 32 is defined by the end wall opposite the end wall 37*a*. In the embodiment depicted in FIG. 3, the dispensing case 32 can include a lid 37*b*. The lid 37*b* can be coupled to the dispensing case 32 in any manner discussed above regarding the lid 36. For example, the lid 37*b* may be coupled to the dispensing case 32 by a hinge 37*c*, which may be a living hinge.

The lid 37*b* can be shifted between an open configuration, where the lid 37*b* permits access to at least a portion of the opening 31*b*, and a closed configuration, where the lid 37*b* substantially blocks the opening 31*b*. FIG. 3 depicts an embodiment of the dispensing case 32 with the lid 37*b* in an open configuration. When the lid 37*b* is in an open configuration, a stack of eyewear articles 34 can be inserted into the dispensing case 32. When the lid 37*b* is in a closed configuration, the lid 37*b* can secure the stack of eyewear articles 34 inside the dispensing case 32. In certain embodiments, the lid 37*b* may include an attachment element 37*d* to maintain the lid 37*b* in a closed configuration. The attachment element 37*d* can include any of the properties discussed above regarding the attachment element 36*e*.

In an embodiment not depicted in FIG. 3, the dispensing case 32 may not include an opening 31*b*. In embodiments where the dispensing case 32 does not include an opening 31*b*, the opening 31*a* may be large enough to allow the insertion of a stack of eyewear articles 34 into the dispensing case 32.

In certain embodiments, the dispensing case 32 may include an object coupling member 39 for coupling the dispensing case 32 to an object, such as, for example, a key chain, a purse, or a bag. In one embodiment, the object coupling member 39 can be a loop that is attached to the side wall 35*a* of the main housing 32*a*. Objects can be coupled to the object coupling member 39 by any manner, such as, for example, by using a key ring, a hook, or a clasp.

The stack of eyewear articles 34 received in the dispensing case 32 includes individual eyewear articles that are in a substantially flat configuration and stacked on top of one another. In certain embodiments, the stack of eyewear articles 34 may include individual eyewear articles with at least one eye cover and one backing. In other embodiments, the stack of eyewear articles 34 may include individual eyewear articles with at least two eye covers and one backing. In embodiments where the individual eyewear articles include at least two eye covers and one backing, the individual articles may be folded and then stacked onto one another or the individual articles may be directly stacked onto one another without folding.

In certain embodiments, the stack of eyewear articles 34 received inside the dispensing case 32 includes at least 5, 10, or 20 eyewear articles in a stacked configuration, and/or not more than 100, 85, or 70 eyewear articles in a stacked configuration.

In the embodiment depicted in FIG. 3, the opening 31*a* is configured to allow at least 1, 2, or 4 eyewear articles, and/or less than 8, 10, or 12 eyewear articles in a stacked configuration to slide through the opening 31*a* at the same time.

When received in the dispensing case 32, a first/top eyewear article of the stack of eyewear articles 34 can be contacted by at least one human finger and slid over the top article of the stack of eyewear articles 34 remaining in the dispensing case 32, and slid through the opening 31*a*. To enable sliding of the first eyewear article over the top eyewear article retained in the dispensing case 32, the frictional force between the finger and the first article should be greater than the frictional force between the bottom surface of the first article and the top surface of the second article of the stack of eyewear articles 34 retained in the dispensing case 32. In certain embodiments, a user can remove as many eyewear articles as necessary at any given time. For example, in one embodiment, a user may need to separately remove two individual eyewear articles. In another embodiment, a user may remove at least two individual eyewear articles at the same time.

Figure 4:
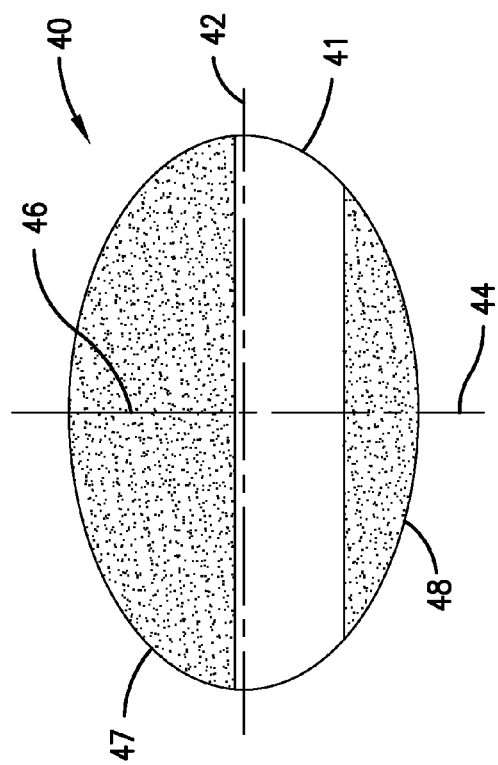
FIG. 4 is a plan view of an eye cover in accordance with one embodiment of the present invention, particularly illustrating the eye cover in a substantially flat configuration having a long axis and a short axis, two separate adhesive zones, and a scission intersecting one of the adhesive zones.

FIG. 4 illustrates a detailed view of one embodiment of an eye cover 40 in a substantially flat configuration. The eye cover 40 has two axes of symmetry: a long axis 42 ($A_L$) and a short axis 44 ($A_S$). The eye cover 40 may have an $A_L:A_S$ ratio of at least 1.25:1, 1.5:1, 1.75:1, or 2:1, and/or not more than 4:1, 3:1, 2.5:1, or 2.25:1. In one or more embodiments, the eye cover 40 is substantially oval in shape.

In certain embodiments, the eye cover 40 may include a film 41 with an adhesive 47 and/or 48 coated thereon. An adhesive 47 and/or 48 may be coated onto the film 41 in any number of patterns. For example, the eye cover 40 can include an adhesive in separate adhesive zones 47 and 48. In the embodiment depicted in FIG. 4, the adhesive zones 47 and 48 each include a strip of adhesive that extends along the long axis 42 of the eye cover 40. The adhesive zone 47 has an area $A_1$ and the adhesive zone 48 has an area $A_2$. In certain embodiments, the ratio of $A_1:A_2$ is at least 1.25:1, 1.5:1, 2:1, or 3:1, and/or not more than 10:1, 8:1, 6:1, or 4:1.

Other embodiments exhibiting different configurations of adhesive coated onto the film 41 are contemplated by this invention, and a specific configuration can be selected by one skilled in the art. For example, in one embodiment, the eye cover 40 may include only one adhesive zone, such as, for example, adhesive zone 47. In another embodiment, the adhesive zones 47 and/or 48 may not extend along the entire length of the eye cover 40. In yet another embodiment, an adhesive zone may include a strip of adhesive that extends along the short axis 44 of the eye cover 40. In certain embodiments, an adhesive may extend along the entire area of the eye cover 40. In one embodiment, the eye cover 40 may not include an adhesive.

The eye cover 40 of FIG. 4 includes a scission 46 that extends from the central portion to the edge of the eye cover 40. In the embodiment depicted in FIG. 4, the scission 46 intersects adhesive zone 47 and extends in a direction parallel to the short axis 44. In certain embodiments, the scission 46 can be collinear with the short axis 44. The scission 46 can be located in any number of positions that are suitable for use in accordance with the present invention, such as, for example, the scission 46 may extend from the central portion to the edge of the eye cover 40, but in a direction that is not parallel to the short axis 44. In one embodiment, the scission 46 can extend from near one edge to the opposing edge of the eye cover 40. In certain embodiments, the eye cover 40 does not include a scission 46.

Figure 5:
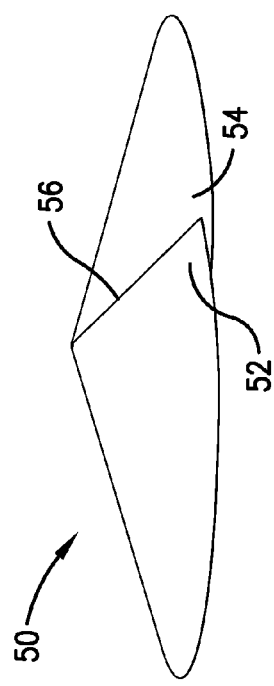
FIG. 5 is a perspective view of an eye cover in accordance with one embodiment of the present invention, particularly illustrating the convex face of the eye cover in an eye-covering configuration with the near scission portions of the eye cover overlapping.

FIG. 5 depicts the convex face of an eye cover 50 that has been shifted from the substantially flat configuration, illustrated in FIG. 4, into a substantially concave eye-covering configuration. As shown in FIG. 5, the eye cover 50 includes two eye cover sections 52 and 54, created by the scission 56 in the eye cover 50. In one embodiment, a user can manipulate the eye cover 50 from the substantially flat configuration into the concave eye-covering configuration by manually forcing the eye cover sections 52 and 54 to overlap. In the embodiment depicted in FIG. 5, the eye-covering configuration of the eye cover 50 includes a near-scission portion of eye cover section 52 overlapping a near-scission portion of eye cover section 54.

In certain embodiments, the eye cover 50 may be maintained in the eye-covering configuration by a fixing element of the eye cover 50. In one embodiment, the fixing element can be a pressure sensitive adhesive coated onto the film of the eye cover 50 that can adhesively attach the overlapping eye cover sections 52 and 54 to one another. In another embodiment, the fixing element can be the same pressure sensitive adhesive coated onto the film of the eye cover 50 that was used to attach the eye cover 50 to a backing, when the eye cover 50 was in a substantially flat configuration. Other fixing elements are contemplated by the present invention. For example, in another embodiment, the fixing element could be a hole or slit in the eye cover 50, where the eye cover section 52 could overlap the eye cover section 54 and engage the hole or slit.

In certain embodiments, the eye-covering configuration of the eye cover 50 may be substantially conical in shape. In one or more embodiments, the eye-covering configuration of the eye cover 50 may be substantially symmetrical. The shape of the eye-covering configuration of the eye cover 50 can vary as long as that shape is suitable to cover a human eye.

Figure 6:
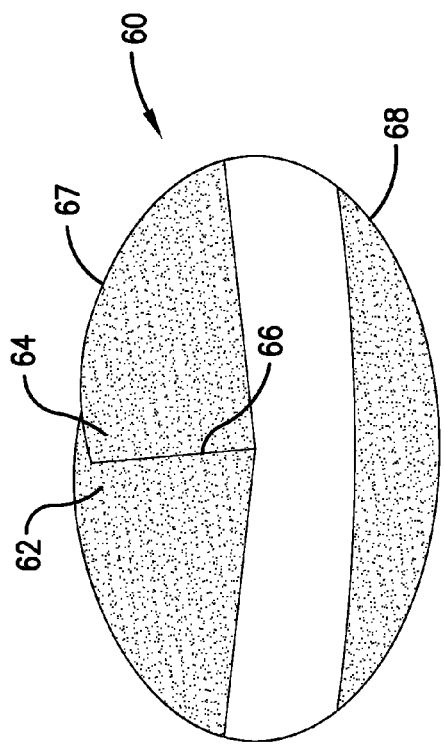
FIG. 6 is a plan view of an eye cover in accordance with one embodiment of the present invention, particularly illustrating the concave face of the eye cover in an eye-covering configuration with two separate adhesive zones and the near scission portions of the eye cover overlapping.

FIG. 6 depicts the concave face of an eye cover 60 in an eye-covering configuration. The eye cover 60 includes a scission 66 and two eye cover sections 62 and 64 on either side of the scission 66. The concave face of the eye cover 60 also includes an adhesive in two separate adhesive zones 67 and 68. In one embodiment, adhesive zone 67 extends along the eye cover section 62 that overlaps and is in contact with the convex face of the eye cover section 64 to thereby maintain the eye cover 60 in a substantially concave eye-covering configuration.

When the eye cover 60 is in the eye-covering configuration and placed over a human eye, the adhesive zones 67 and 68 may contact the region surrounding the eye to secure the eye cover 60 to the user's face. In other embodiments not depicted in FIG. 6, the eye cover 60 may not include an adhesive and, when in an eye-covering configuration, may still remain secured over a user's eyes. In certain embodiments, the eye cover 60, when in the eye-covering configuration and placed over a human eye, provides space for the user's eyelid to move and/or to remain open for the user to see their surrounding environment.

In one embodiment, in order to protect a user's eyes, a user may need to slide an eyewear article out of a dispensing case, remove the backing from the eye cover, manipulate the eye cover into an eye-covering configuration, place the eye cover in the eye-covering configuration over their eye, and repeat these steps for their other eye.

In certain embodiments, the eyewear articles are designed for one time use and are disposable. For example, when the user no longer needs to protect their eyes from an external environment, the eye covers can be removed from their eyes and discarded along with the separated backings.

It is the inventor's intent to rely on the Doctrine of Equivalents to determine and assess the reasonably fair scope of the present invention as it pertains to any methods and systems not materially departing from but outside the literal scope of the invention as set forth in the following claims.

What is claimed is:

1. A portable eye protection system comprising:
a dispensing case comprising:
a main housing having a top face, a bottom face, two sidewalls, and an endwall;
a first opening at least partly defined by said top face and said endwall;
a first lid shiftable between a first open configuration where said first lid permits access to at least a portion of said first opening and a first closed configuration where said first lid substantially blocks said first opening;
a first attachment element for maintaining said first lid in said first closed configuration;
a first hinge for coupling said first lid to said main housing;
a second hinge for folding a portion of said first lid in said first closed configuration to at least partially block a portion of said first opening defined by said top face;
a second opening substantially opposite said endwall;
a second lid shiftable between a second open configuration where said second lid permits access to at least a portion of said second opening and a second closed configuration where said second lid substantially blocks said second opening,
said second lid comprising a third hinge for coupling said second lid to said main housing and a second attachment element for maintaining said second lid in said second closed configuration; and
a plurality of substantially flat, individually-dispensable eyewear articles received in said dispensing case and configured for individual manual removal from said main housing through said first opening,
wherein each of said individually-dispensable articles comprises a backing and an eye cover removably attached to said backing, wherein said eye cover is configured to be shifted from a substantially flat configuration into a substantially concave eye-covering configuration when said eye cover is removed from said backing;
wherein said endwall is configured to resist removal of at least one of said plurality of substantially flat eyewear articles during individual manual removal of another of said substantially flat eyewear articles.

2. The portable eye protection system according to claim 1, wherein said substantially flat eyewear articles are in a stacked configuration when inside said dispensing case, wherein said dispensing case is configured to hold at least 5 of said eyewear articles in said stacked configuration.

3. The portable eye protection system according to claim 1, wherein each of said top and bottom faces have an area of less than 5 square inches, wherein the main housing has a thickness, measured between the top and bottom faces, of less than 1 inch.

4. The portable eye protection system according to claim 1, wherein said eye cover is substantially oval in shape when in said substantially flat configuration.

5. The portable eye protection system according to claim 1, wherein said eye cover comprises a fixing element for maintaining said eye cover in said eye-covering configuration.

6. The portable eye protection system according to claim 5, wherein said fixing element comprises a pressure sensitive adhesive.

7. The portable eye protection system according to claim 1, wherein said eye cover comprises a central portion, an edge, and a scission extending from said central portion to said edge when said eye cover is in said substantially flat configuration.

8. The portable eye protection system according to claim 7, wherein portions of said eye cover located near said scission overlap when said eye cover is in said eye-covering configuration.

9. The portable eye protection system according to claim 8, wherein said eye cover comprises an adhesive located near said scission, wherein said adhesive attaches and holds the overlapping portions of said eye cover to one another when said eye cover is in said eye-covering configuration.

10. The portable eye protection system according to claim 1, wherein said eye cover comprises a film and an adhesive coated onto said film, wherein at least a portion of said adhesive adheres to said backing when said eye cover is in said substantially flat configuration.

11. The portable eye protection system according to claim 10, wherein at least a portion of said adhesive holds said eye cover in said eye-covering configuration.

12. The portable eye protection system according to claim 1, wherein said eye cover comprises a transparent film having a spectral transmittance value greater than 0.01 for wavelengths greater than 400 nm.

13. The portable eye protection system according to claim 1, wherein said eye cover comprises a UV-blocking film configured to block at least a portion of radiation having a wavelength of from 200 nanometers to 400 nanometers.

* * * * *